United States Patent
Winters

[11] Patent Number: 6,123,711
[45] Date of Patent: Sep. 26, 2000

[54] TISSUE FIXATION DEVICE AND METHOD

[76] Inventor: Thomas F. Winters, 2031 Venetian Way, Winter Park, Fla. 32789

[21] Appl. No.: 09/329,563

[22] Filed: Jun. 10, 1999

[51] Int. Cl.⁷ ............................ A61B 17/56; A61B 17/58; A61F 2/30

[52] U.S. Cl. ................................................................ 606/73

[58] Field of Search ................... 606/65, 66, 69, 606/71, 72, 73, 75; 623/13

[56] References Cited

U.S. PATENT DOCUMENTS

| | | | |
|---|---|---|---|
| 4,870,957 | 10/1989 | Goble et al. | 606/73 |
| 4,988,351 | 1/1991 | Paulos et al. | 606/75 |
| 5,013,316 | 5/1991 | Goble et al. | 606/72 |
| 5,062,843 | 11/1991 | Mahony, III . | |
| 5,108,431 | 4/1992 | Mansat et al. . | |
| 5,129,902 | 7/1992 | Goble et al. | 606/72 |
| 5,314,427 | 5/1994 | Goble et al. | 606/72 |
| 5,352,229 | 10/1994 | Goble et al. | 606/72 |
| 5,383,878 | 1/1995 | Roger et al. . | |
| 5,403,136 | 4/1995 | Mathys | 606/73 |
| 5,425,767 | 6/1995 | Steininger et al. . | |
| 5,454,811 | 10/1995 | Huebner . | |
| 5,571,184 | 11/1996 | DeSatnick . | |
| 5,575,819 | 11/1996 | Amis | 623/16 |
| 5,601,558 | 2/1997 | Torrie et al. . | |
| 5,632,748 | 5/1997 | Beck, Jr. et al. . | |
| 5,702,398 | 12/1997 | Tarabishy | 606/72 |
| 5,718,706 | 2/1998 | Roger | 606/73 |
| 5,766,250 | 6/1998 | Chervitz et al. | 623/13 |

FOREIGN PATENT DOCUMENTS

| | | |
|---|---|---|
| 0 232 049 | 8/1987 | European Pat. Off. . |
| 0 317 406 | 5/1989 | European Pat. Off. . |

*Primary Examiner*—Gene Mancene
*Assistant Examiner*—Eduardo C. Robert
*Attorney, Agent, or Firm*—Allen, Dyer, Doppelt, Milbrath & Gilchrist, P.A.

[57] ABSTRACT

A system for fixing soft tissue within a bone tunnel includes a first fixation member that is adapted for insertion upon a piece of soft tissue positioned within a bone tunnel, with a portion of the soft tissue emerging therefrom. A second fixation member is adapted to engage the first fixation member at its proximal end and is restrainable against disengagement therewith. The proximal end has an element for engaging the soft tissue. In a particular embodiment the first fixation member includes a screw having a bore extending from the proximal end and the second fixation member has a distal post portion adapted for mating with the bore and driving the screw rotationally thereby. The second fixation member may include a tack member and a barbed washer that is rotatable about the post and retainable by a head portion on the tack member. The barbs on the washer are for engaging and restraining a movement of the soft tissue outside the bone tunnel. Alternatively, the second fixation member may include a tack-type element that has a barbed head. In another embodiment a cannula capable of restraining the washer against rotation is used to guide the screw into the bone tunnel.

29 Claims, 11 Drawing Sheets

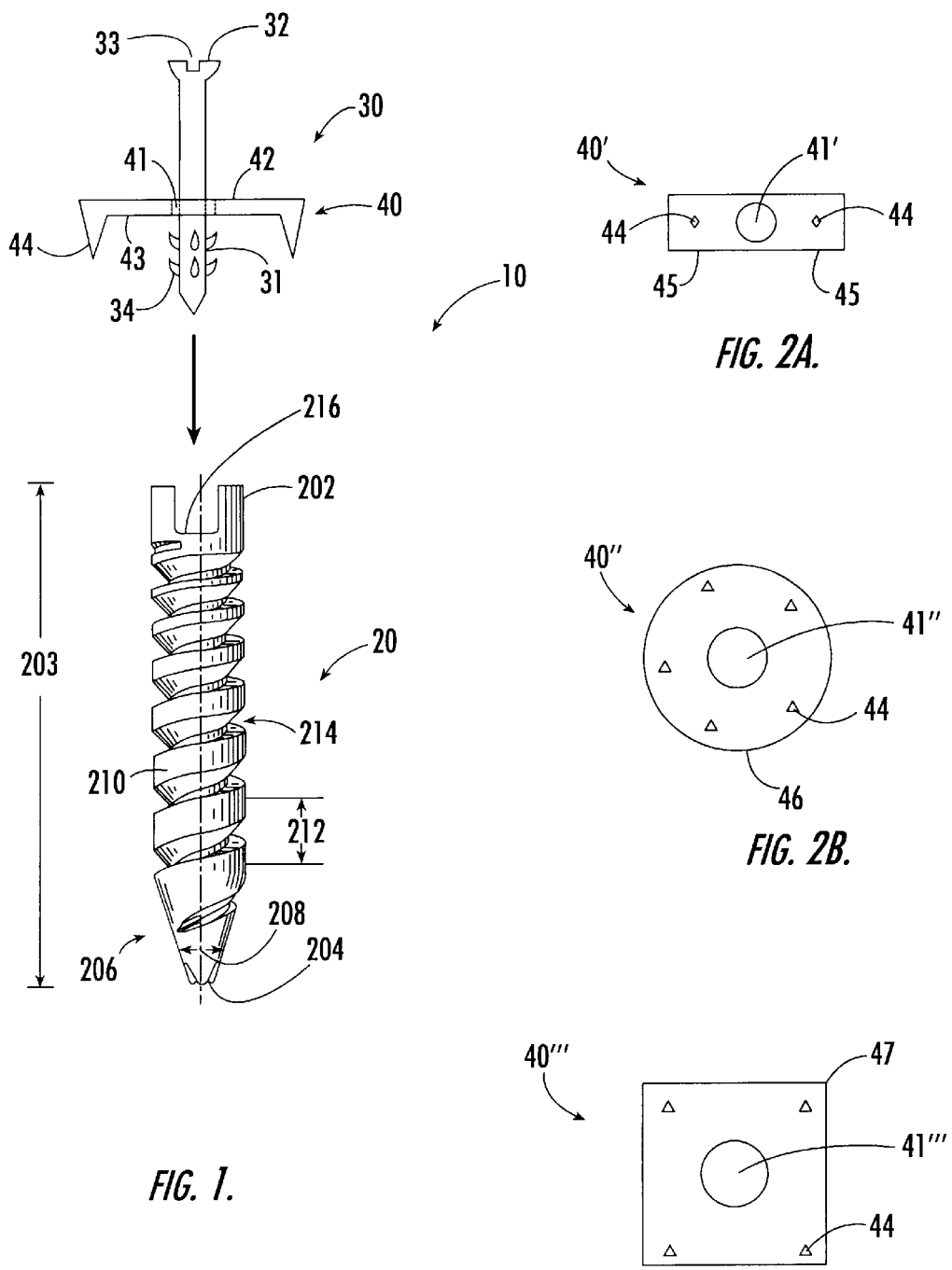

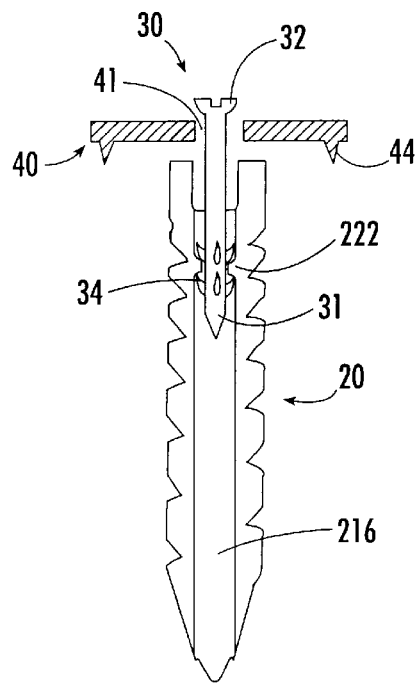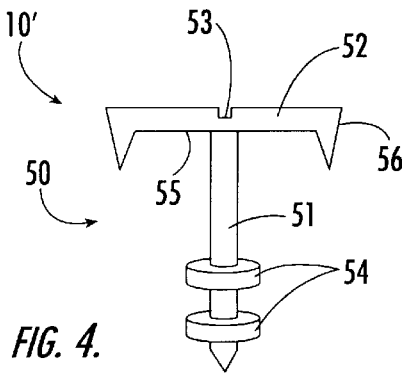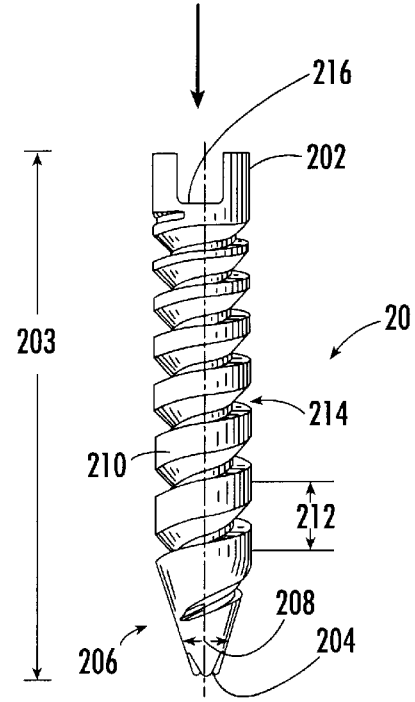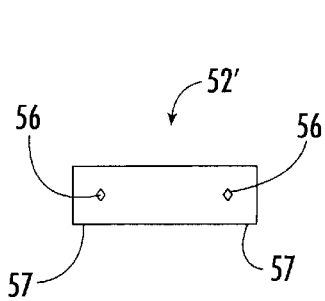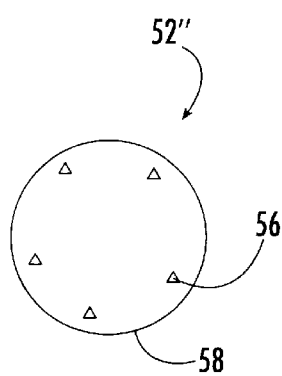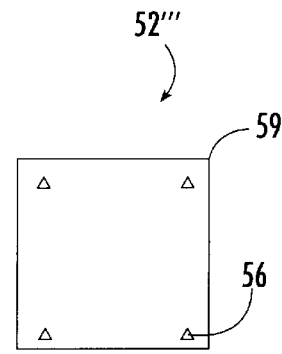

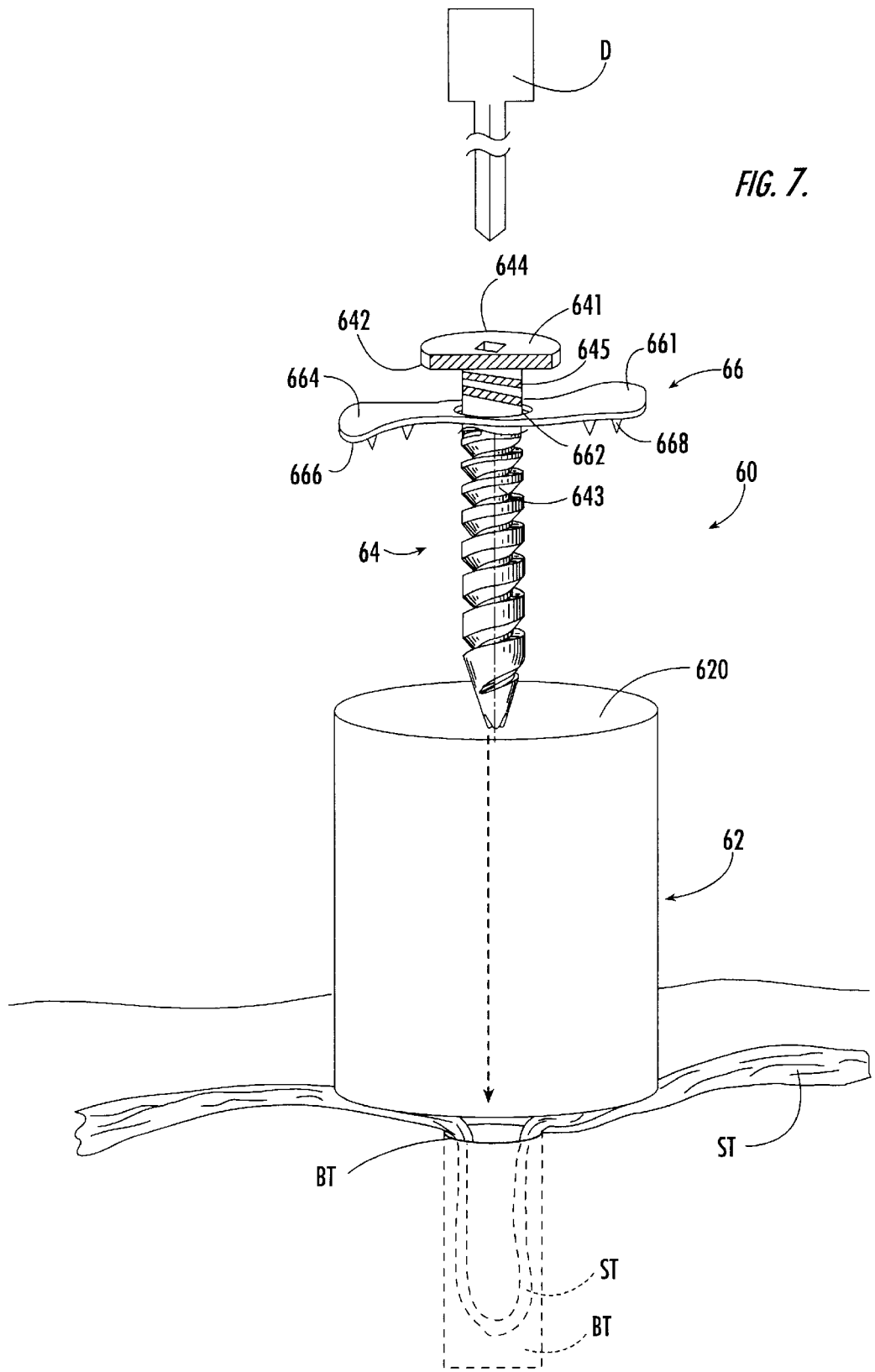

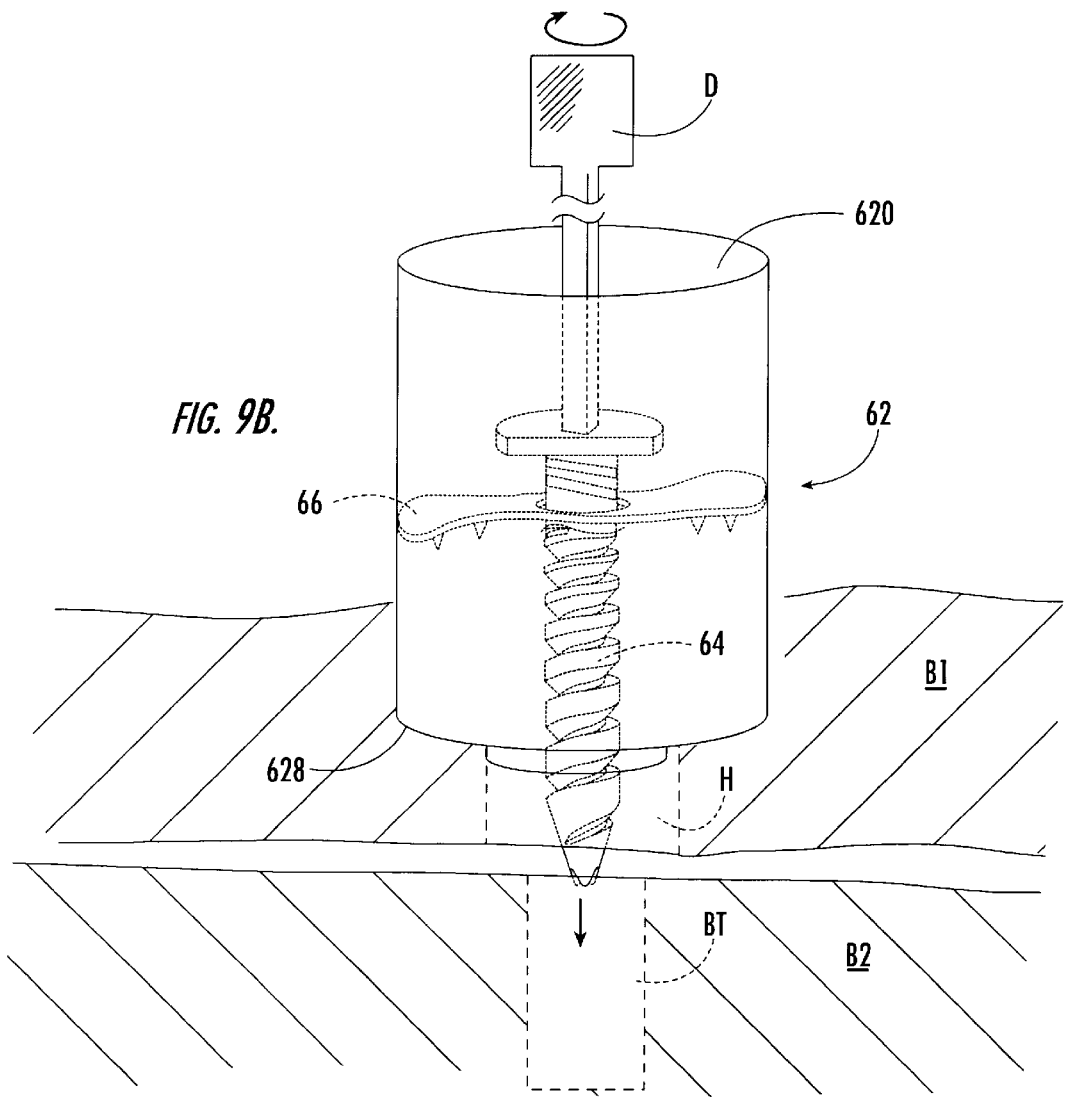

TISSUE FIXATION DEVICE AND METHOD

BACKGROUND OF THE INVENTION

1. Field of the Invention

The present invention relates to surgical devices and methods for affixing two sections of tissue together, and, more particularly, to a device and method for affixing a piece of soft tissue to a bone or affixing two pieces of bone together.

2. Description of Related Art

Orthopedic surgical procedures sometimes require an attachment (or reattachment) of a flexible member to a bone. The flexible member might comprise soft tissue such as a ligament or tendon, a synthetic element, or suture. Devices and methods are known in the art to accomplish such an attachment, including those for affixing the flexible member within a hole of the bone.

For example, it is known to use a member such as a screw to press at least one end of the flexible member against the interior wall of a bone space (Mahony, U.S. Pat. No. 5,062,843; Roger et al., U.S. Pat. No. 5,383,878; Steininger et al., U.S. Pat. No. 5,425,767; Huebner, U.S. Pat. No. 5,454,811; Laboureau, EU 0 317 406). It is also known to anchor a ligament between two elements, the inner one deformable (U.S. Pat. No. 5,108,431), and to pass a ligament through a center of a device, creating tension by relative movement of elements (DeSatnick, U.S. Pat. No. 5,571,184).

A particular surgery in which flexible member attachment is required is endosteal fixation, wherein the terminal ends with bone plugs of an anterior cruciate ligament graft replacement material are attached within bone tunnels. The attachment is often achieved by compressive or interference fit means.

Other such surgeries includes rotator cuff and SLAP lesion repairs.

In addition, it is known to affix two bone sections together, which at present is accomplished with bone screws and/or cabling.

SUMMARY OF THE INVENTION

It is an object of the present invention to provide a system and method for affixing a piece of soft tissue to a bone.

It is a further object to provide such a system that has an element for securing the soft tissue piece within a bone tunnel and another element for securing another portion of the soft tissue against the outside of the bone tunnel.

It is an additional object to provide a system and method for affixing two pieces of bone together.

These and other objects are attained with the system and method of the present invention. A particular embodiment of the system is for fixing soft tissue within a bone tunnel and comprises a first fixation member that has a proximal end and a distal end and is adapted for insertion upon a piece a first portion of soft tissue positioned within a bone tunnel. A second portion of the soft tissue is positioned to emerge from the bone tunnel. A second fixation member is adapted to engage the first fixation member at its proximal end. The second fixation member has means for restraining disengagement with the first fixation member and a proximal end, which has means for engaging the soft tissue's second portion. In an embodiment the first fixation member comprises a screw-type member having a bore extending from the proximal end and the second fixation member has a distal post portion adapted for mating with the bore and driving the screw rotationally thereby.

In a first subembodiment, the second fixation member comprises a tack member and a barbed washer that is rotatable about the post and retainable by a head portion on the tack member. The barbs on the washer are for engaging and restraining a movement of the soft tissue outside the bone tunnel.

In a second subembodiment, the second fixation member comprises a tack-type element that has a barbed head. As above, the barbs are for engaging and restraining the soft tissue outside the bone tunnel.

An alternate embodiment of the invention includes a system for affixing a piece of tissue to a bone, which may comprise affixing soft tissue to bone or two pieces of bone together. This system comprises a generally cylindrical cannula member that is adapted for insertion through the tissue piece and into a tunnel in the bone.

A generally cylindrical screw member is dimensioned for insertion through the cannula member, the screw member having a head at a proximal end and a bore extending at least partially therethrough from the proximal end. The bore has means for being driven by a driver.

A barbed washer has a hole extending from a proximal face through to a distal face. The hole is dimensioned for free rotation about the screw member and for retention by the screw head therebeneath. The distal face has a plurality of barbs extending generally distalward for engaging and restraining a movement of the distal tissue piece.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 illustrates a first embodiment of the fixation system having a barbed washer.

FIGS. 2A–2C are axial cross-sectional views of different subembodiments of the washer of FIG. 1.

FIG. 3 is a longitudinal cross-sectional view of the device of FIG. 1 illustrating the mating of the tack and the screw.

FIG. 4 illustrates a second embodiment of the fixation system having a barbed tack head.

FIGS. 5A–5C are axial cross-sectional views of different subembodiments of the tack head of FIG. 4.

(FIG. 6B) inserting the tack into the screw bore; and (FIG. 6C) impaling the soft tissue on the barbs outside the bone tunnel.

FIG. 7 illustrates an exploded view of a third embodiment of the system using a cannula for guiding the screw.

FIG. 8B: delivering the screw to the bone tunnel; and FIG. 8C: removing the cannula and permitting the barbs to bear against the soft tissue.

FIGS. 9A–9C illustrate the method of using the embodiment of FIG. 7 to affix two pieces of bone together, including, FIG. 9A: inserting the cannula into the first bone piece and inserting the screw and washer into the cannula; FIG. 9B: delivering the screw to the second bone tunnel; and FIG. 9C: removing the cannula and permitting the barbs to bear against the first bone.

DETAILED DESCRIPTION OF THE PREFERRED EMBODIMENTS

Figure 6A:
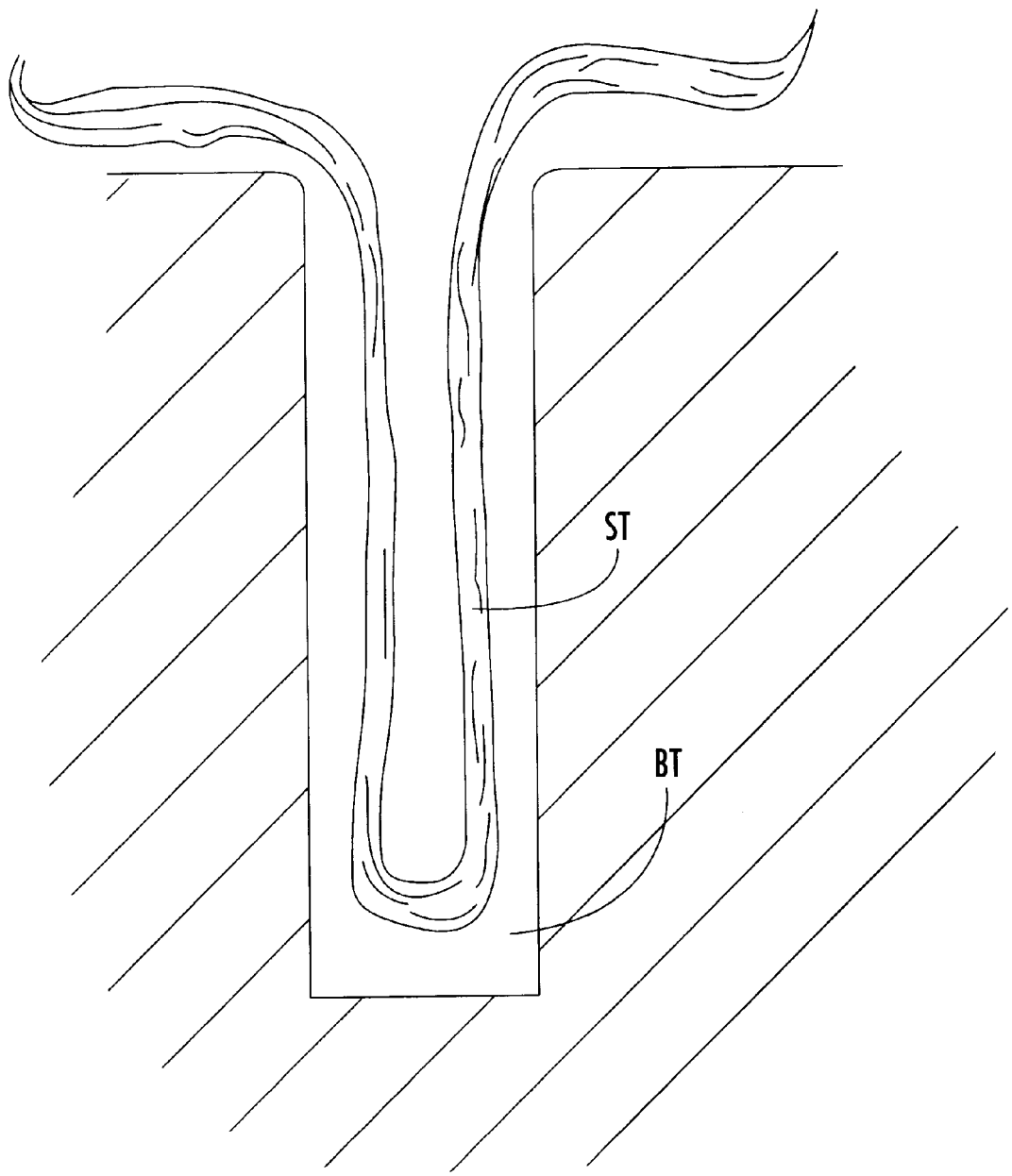
FIGS. 6A–6C illustrate the method of the present invention, including (FIG. 6A) inserting the screw into the bone tunnel atop a piece of soft tissue.

A description of the preferred embodiments of the present invention will now be presented with reference to FIGS. 1–9C.

An exemplary embodiment of the present invention comprises a system 10 including a first and a second fixation member and methods for affixing a piece of soft tissue ST within a bone tunnel BT in a patient. The first fixation member comprises a screw 20 such as has been previously disclosed in U.S. Pat. Nos. 5,503,634 and 5,730,744, the disclosures of which are incorporated herein by reference, although these particular embodiments are not intended as limitations.

The screw 20 has a proximal end 202, a distal end 204, and a length 203. Screw 20 further has a distal portion 206 having a narrowing cross section 208 toward distal end 204, in this specific embodiment the distal portion 206 forming a cone. Alternatively, a self-tapping distal portion could be implemented. In use an insertion of screw 20 into soft tissue is facilitated by the conical-shaped distal portion 206.

Along a central portion 214 between proximal end 202 and distal end 204, screw 20 has a variable-pitch helical protrusion 210. The helical pitch 212 along central portion 214 decreases from distal end 204 to proximal end 202. In use the decrease in helical pitch 212 serves to compress the soft tissue ST within the bone tunnel BT as screw 20 is advanced into the bone tunnel BT in a screwing motion.

The screw material in the preferred embodiment comprises a biodegradable plastic biocompatible with the soft tissue of the patient. Exemplary materials include a nontoxic blend of polycaprolactone and polyglycolide, a blend of polylactide and polyglycolide, pure polydioxanone, poly(ethylene oxide):poly(butylene terephthalate), polyorthoester, polyhydroxybutyrate, or cross-linked collagen. The material is designed to be sufficiently flexible and strong to withstand natural movement during healing. The material is also designed to be biodegradable within a first time span greater than or equal to a second time span over which the soft tissue ST can attach to the bone tunnel BT. In other words, the material is resorbed over a time span commensurate with the healing process, so that, once the soft tissue ST is attached, the screw 20 can gradually degrade, leaving an attached piece of soft tissue ST with no foreign material embedded therein.

In the preferred embodiment, screw 20 further has an axial bore 216. Bore 216 proceeds from proximal end 202 to distal end 204, and has a noncircular cross-sectional shape to permit an elongated post having a noncircular cross-sectional shape to pass into bore 216 and to advance screw 20 into the soft tissue ST by being rotated in a direction having a handedness commensurate with the helically shaped protrusion 210. The cross-sectional shape may, for example, be triangular or square, although these shapes are not intended as limitations.

Screw 20 further has a lip 222 projecting within the bore 216 for restraining barbs passing therebeyond (FIG. 3), as will be discussed in the following.

The second fixation member in a first embodiment comprises a tack 30 having a distal post portion 31 dimensioned for insertion into the screw's bore 216 and a proximal head portion 32 having a width greater than the width of the post portion 31. The tack's head 32 has means for being driven by a driver, such as an indentation 33 adapted for being driven by a driver having a commensurately shaped protrusion.

The tack 30 also has means for being restrained from disengagement with the screw's bore 216. In the embodiment shown in FIGS. 1 and 3, the restraining means comprises a protrusion extending outwardly from the post portion 31 engageable with the lip 222. In particular, the protrusion comprises a plurality of rows of generally proximally extending barbs 34. When at least one row of barbs 34 passes the lip 222 within the screw's bore 216, they are structurally restrained against proximal movement.

The second fixation member further comprises a barbed washer 40 that has a hole 41 extending from a proximal face 42 through to a distal face 43. The hole 41 is dimensioned for free rotation about the post 31 and thus is decoupled in at least one degree of freedom from the tack 30. The hole 41 is further dimensioned for retention by the tack's head portion 32 therebeneath. The distal face 43 has a plurality of barbs 44 extending generally distalward for engaging and retraining a movement of the soft tissue piece outside the bone tunnel BT.

Several embodiments of the washer 40 may be contemplated, although these are not intended as limitations: a generally rectangular shape 40' in axial cross section having two wings 45, a barb 44 extending from each wing (FIG. 2A); a generally circular shape 40" in axial cross section, the barbs 44 extending circumferentially about an edge 46 thereof (FIG. 2B); and a generally square shape 40'" in axial cross section, the barbs extending from adjacent each corner 47 thereof.

A second embodiment of the system 10' (FIGS. 4–5C) comprises a tack 50 having a distal post portion 51 dimensioned for insertion into the screw's bore 216 and a proximal head portion 52 having a width greater than the width of the post portion 51. The tack's head 52 has means for being driven by a driver, such as an indentation 53 adapted for being driven by a driver having a commensurately shaped protrusion.

The tack 50 also has means for being restrained from disengagement with the screw's bore 216. In the embodiment shown in FIG. 4, the restraining means comprises a protrusion extending outwardly from the post portion 51 engageable with the lip 222. In a particular embodiment, the protrusion comprises a plurality of generally annular deformable rings 54 that have sufficient flexibility to be pushed past the lip 222 but restrain removal in a proximal direction.

The tack's head 52 has a distal face 55 that has a plurality of barbs 56 extending generally distalward for engaging and retraining a movement of the soft tissue piece outside the bone tunnel BT.

Several embodiments of the head 52 may be contemplated, although these are not intended as limitations: a generally rectangular shape 52' in axial cross section having two wings 57, a barb 56 extending from each wing (FIG. 5A); a generally circular shape 52" in axial cross section, the barbs 56 extending circumferentially about an edge 58 thereof (FIG. 5B); and a generally rectilinear shape 52'" in axial cross section, the barbs 56 extending from adjacent each corner 59 thereof.

Figure 6B:
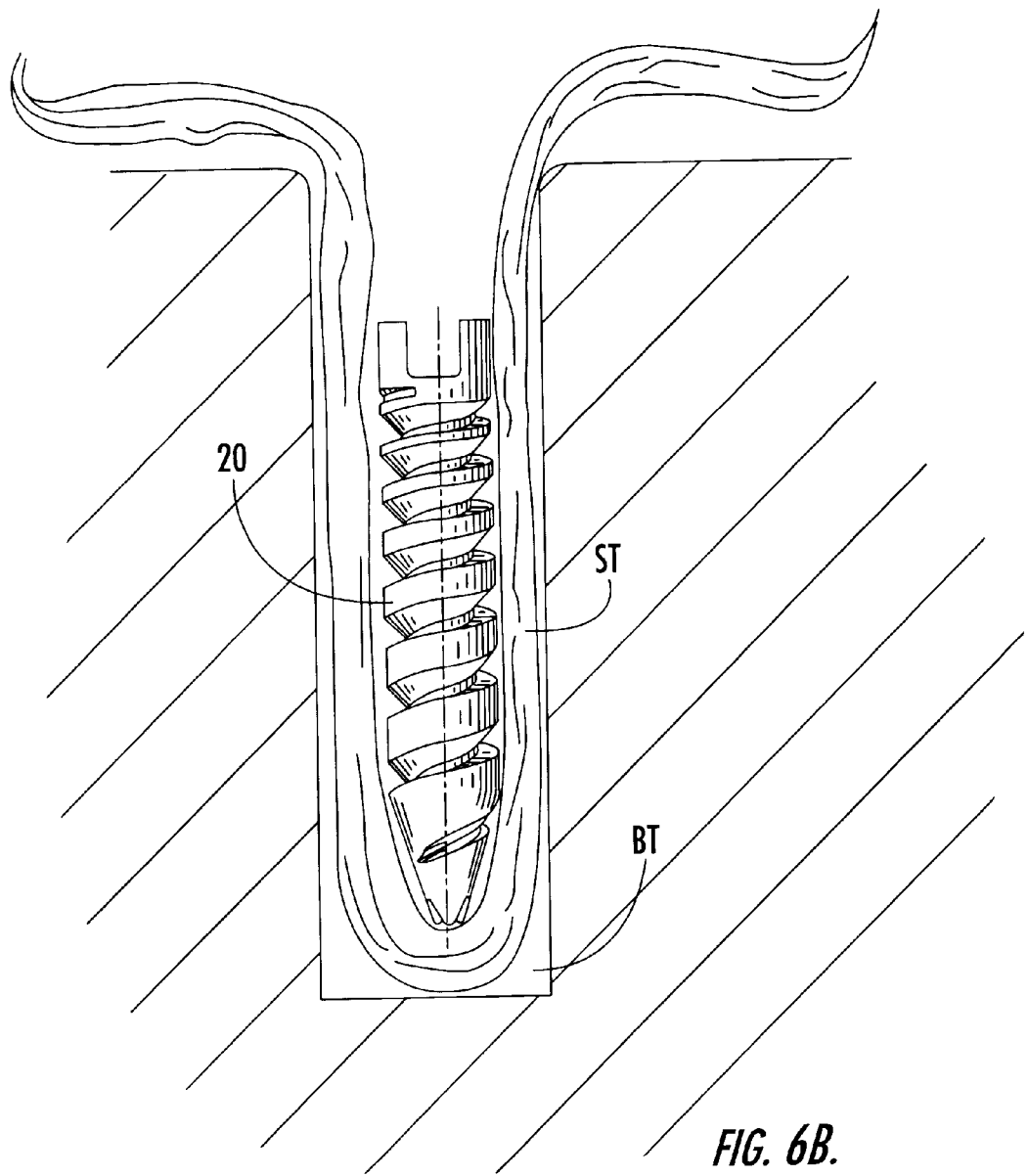
Figure 6C:
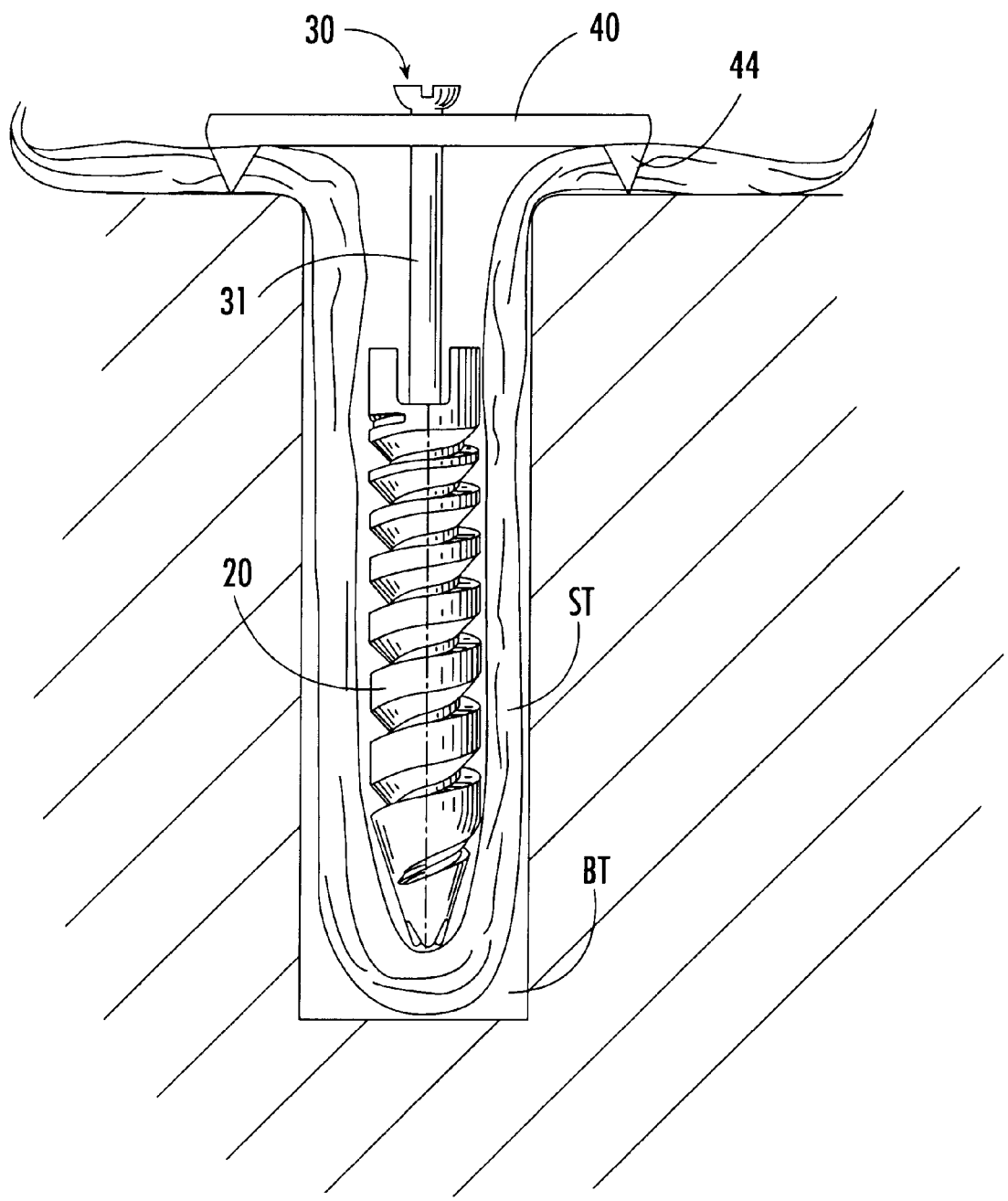

A method of using the devices (FIGS. 6A–C, shown for system 10) of the present invention to affix a piece of soft tissue ST within a bone tunnel BT comprises the step of positioning a piece of soft tissue ST so that a portion thereof resides within the bone tunnel BT. Next a first fixation member such as a screw 20 is positioned upon the piece of soft tissue ST within the bone tunnel BT (FIG. 6A), for example, using the cannula system described in U.S. Pat. Nos. 5,503,634 and 5,730,744 (not shown here).

The distal post portion 31 of the tack 30 is then engaged with a proximal portion of the screw 20, specifically, the post 31 is inserted into the screw's bore 216 until at least some of the barbs 34 pass the lip 222 and are restrained thereby from disengagement. In this embodiment the tack 30 is screwed into the screw's bore 216, while the washer 40 is permitted to spin with respect to the tack 30, thus avoiding engagement of the soft tissue ST by the washer's barbs 44 until desired.

A piece of the soft tissue ST outside the bone tunnel BT is then impaled upon the washer's barbs 44, which serves to provide additional fixation of the soft tissue ST.

A third embodiment of the system 60 (FIG. 7) is useful for affixing a piece of soft tissue ST within a bone tunnel BT or for affixing two pieces of bone B1,B2 together. The system 60 includes a cannula 62 that is adapted for insertion into the surgical site adjacent a bone tunnel BT. The cannula 62 is generally cylindrical and has a longitudinal bore 620 therethrough from a proximal end 621 to a distal end 622.

The screw 64, which is similar in construction to screw 20 above, is generally cylindrical and is dimensioned for insertion through the cannula 62. The screw 64 has a head 641 at a proximal end 642, a threaded distal shaft portion 643, and a bore 644 extending at least partially therethrough from the proximal end 642. The bore 644 has a square shape for being driven by a commensurately shaped square driver D. Adjacent the head 641 is a reverse-threaded shaft portion 645.

A barbed washer 66 has a hole 662 extending from a proximal face 664 through to a distal face 666. The hole 662 is dimensioned for free rotation about the screw's shaft 643 and for retention by the screw head 641 therebeneath. The hole 662 also is reverse threaded for engaging the reverse-threaded portion 645 of the screw's shaft 643. The distal face 666 has a plurality of barbs 668 extending generally distalward for engaging and retraining a movement of the distal tissue piece ST or B1.

The washer 66 also has a flexible head that has a pair of outwardly extending wings 661, and the barbs 668 extend distal of each wing 661.

The screw 64 and washer 66 are dimensioned to pass through the cannula bore 620.

This embodiment 60 may be used either to affix soft tissue to bone or two pieces of bone together, as in the methods illustrated in FIGS. 8A–8B and 9A–9C. In the first, a piece of soft tissue ST is positioned with a first portion within a bone tunnel BT and a second portion extending therefrom. A cannula 62 is inserted into the surgical site with its distal end 628 positioned adjacent the bone tunnel BT and against the soft tissue's ST second portion (FIG. 7).

Figure 8A:
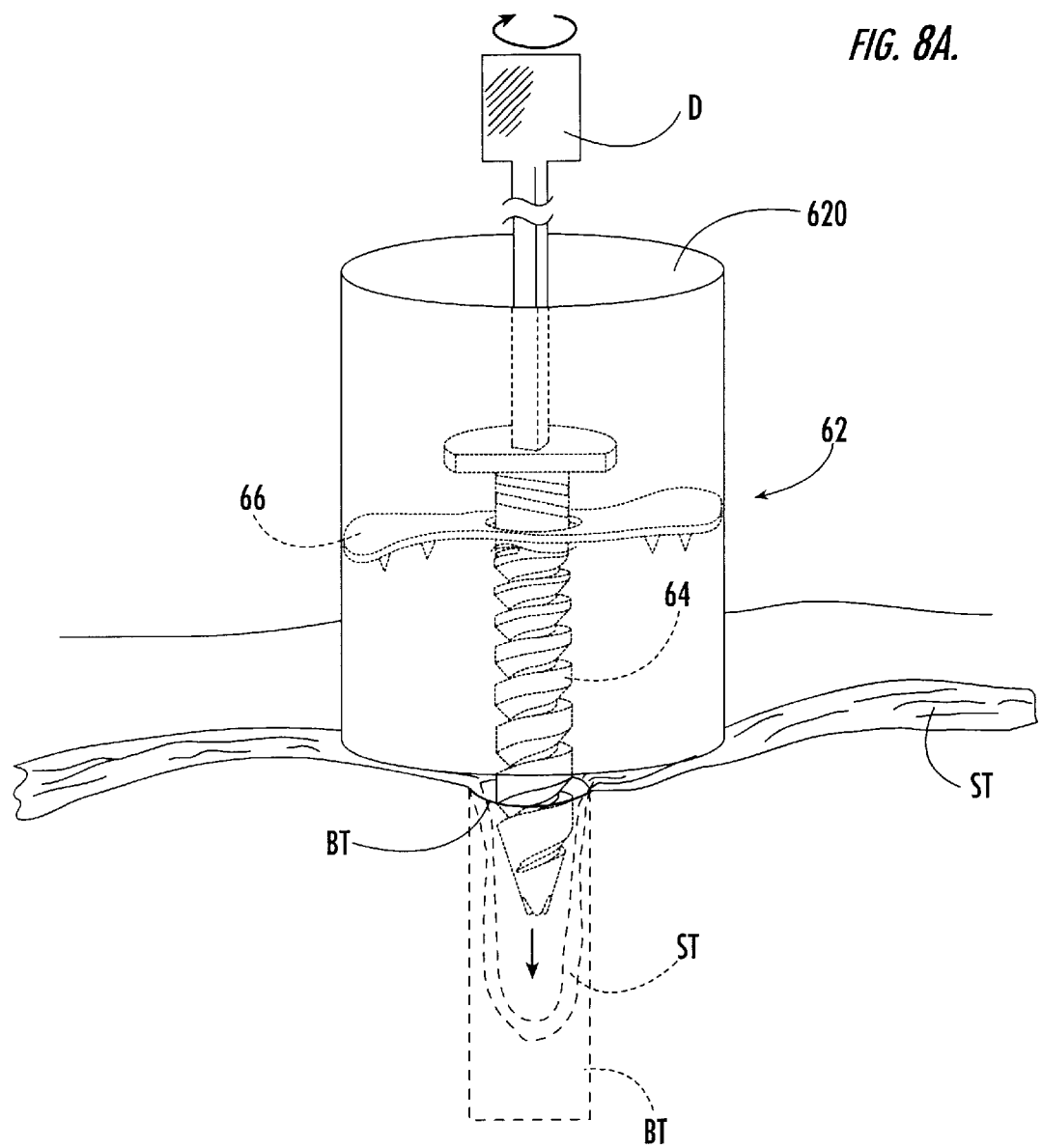
FIGS. 8A–8B illustrate the method of using the embodiment of FIG. 7 to affix soft tissue within a bone tunnel, including.

A screw 64 is inserted through the hole 662 in the washer 66, and the screw 64 and washer 66 assemblage is inserted into the cannula 62 (FIG. 7). The screw 64 is driven into the bone tunnel BT and against the soft tissue ST, with the washer 66 permitted to spin against the screw 64 while being retained within the cannula's proximal portion 622 (FIG. 8A).

Figure 8B:
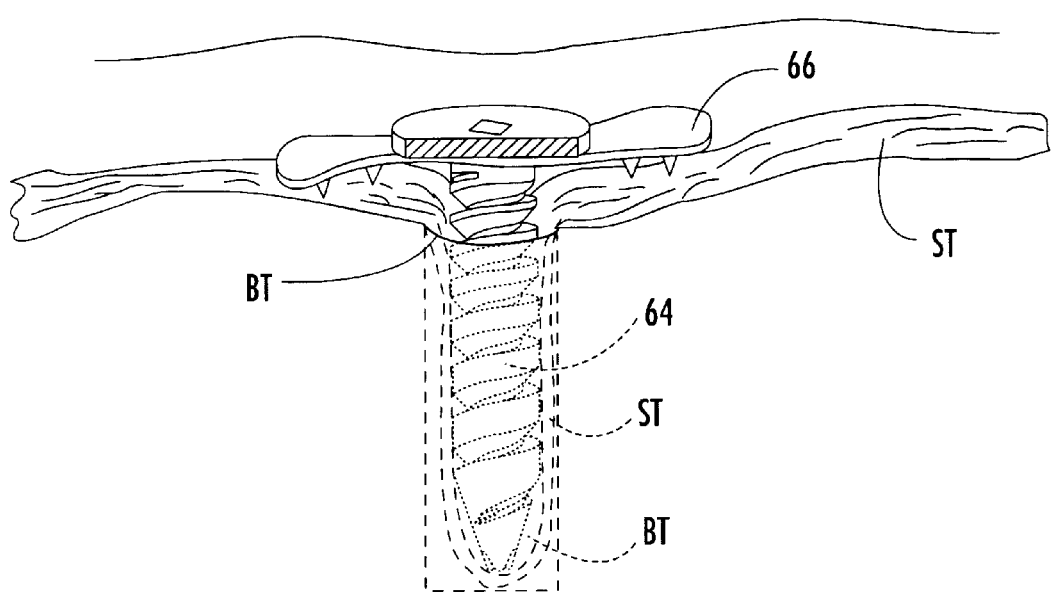

Next the cannula 62 is removed from the surgical site, and the barbs 663 are permitted to bear against the soft tissue's ST second portion adjacent the tunnel BT (FIG. 8B).

In the second method using the system 60, a distal B2 and a proximal B1 piece of bone are affixed together. This method comprises the steps of making a hole H through the proximal bone piece B1. Next a tunnel BT is made in the distal bone piece B2.

Figure 9A:
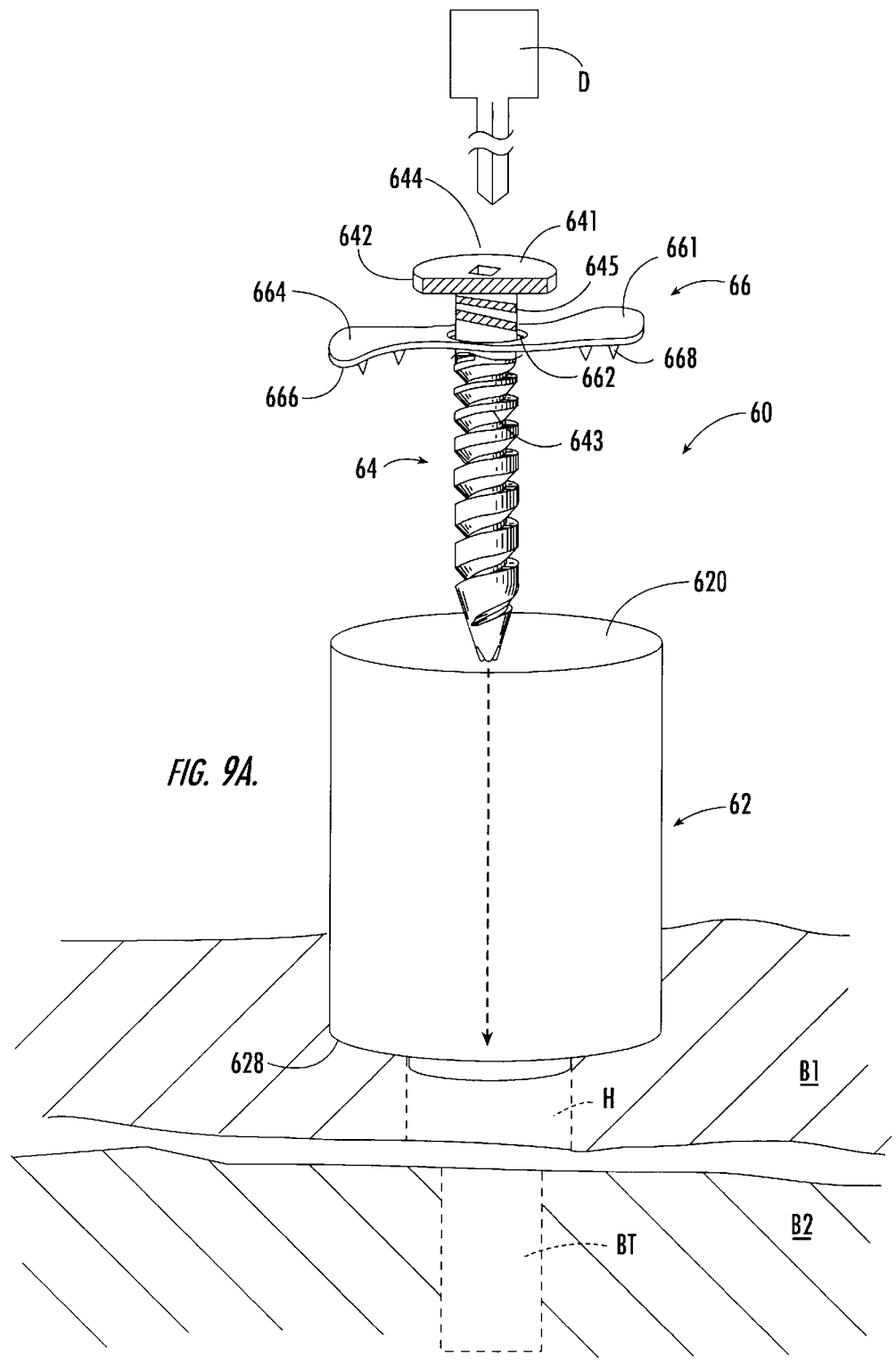

The cannula 62 is positioned with a distal end 628 adjacent the proximal bone piece hole H. A screw 64 and washer 66 assemblage is inserted into the cannula 62 (FIG. 9A). The screw 64 is driven into the distal bone piece tunnel BT, with the washer 66 permitted to spin against the screw 64 while being retained within the cannula's proximal portion 622 (FIG. 9B).

Figure 9C:
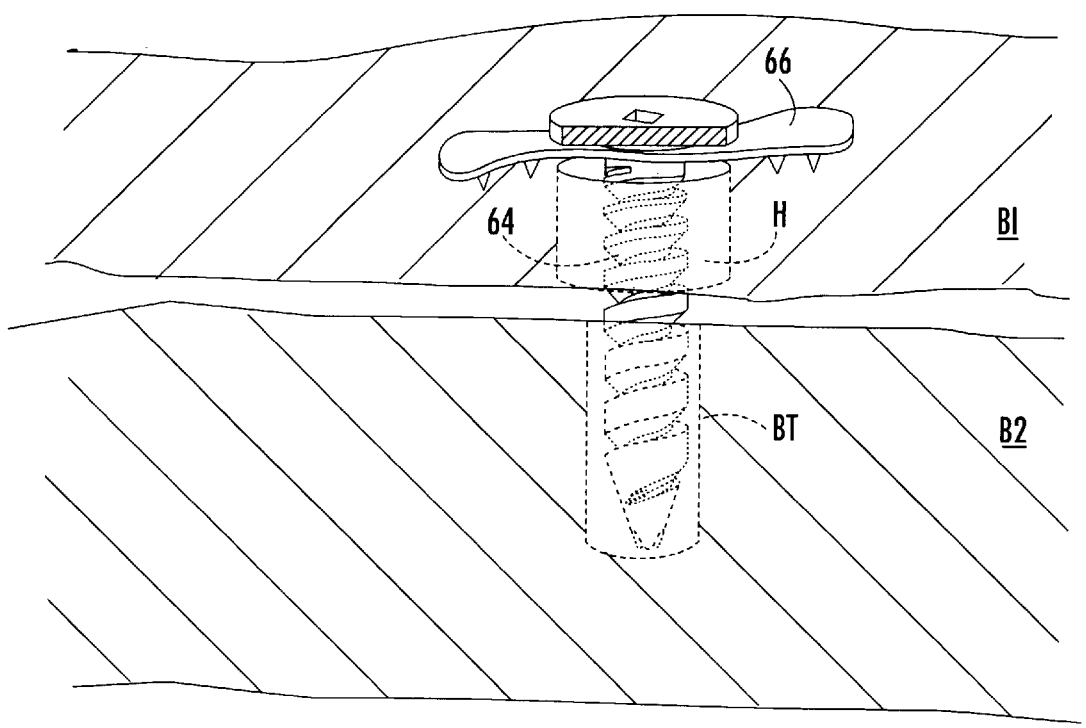

Then the cannula 62 is removed from the proximal bone piece hole H, and the barbs 663 are permitted to bear against the proximal bone portion B1 adjacent the hole H (FIG. 9C).

It may be appreciated by one skilled in the art that additional embodiments may be contemplated, including screws, systems, and methods for affixing other flexible members into tunnels, such as in the artificial ligaments and tendons and suture.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A system for fixing soft tissue within a bone tunnel comprising:

a first fixation member having a proximal end and a distal end and adapted for insertion against a first portion of soft tissue positioned within a bone tunnel, a second portion of the soft tissue emerging from the bone tunnel; and a second fixation member adapted to engage the first fixation member at the proximal end thereof, the second fixation member having means for restraining disengagement therewith and a proximal end having means for engaging the soft tissue second portion, wherein the second fixation member when engaged with the first fixation member is decoupled in at least one degree of freedom therefrom.

2. The fixation system recited in claim 1, wherein the first fixation member comprises a screw-type member having a bore extending at least partially therethrough from the proximal end, the bore having means for being driven by the second fixation member.

3. The fixation system recited in claim 2, wherein the second fixation member comprises:

a tack member having a distal post portion dimensioned for insertion into the screw member bore and a proximal head portion having a width greater than a width of the post portion; and a barbed washer having a hole extending from a proximal face through to a distal face, the hole dimensioned for free rotation about the post and for retention by the tack head portion therebeneath, the distal face having a plurality of barbs extending generally distalward for engaging and restraining a movement of the soft tissue piece.

4. The fixation system recited in claim 3, wherein the tack member head portion has means for being driven by a driver.

5. The fixation system recited in claim 3, wherein the restraining means comprises a protrusion extending outwardly from the post portion and the screw-type member bore has a protruding lip therein adapted to restrainingly engage the protrusion.

6. The fixation system recited in claim 5, wherein the protrusion comprises a plurality of generally proximally extending barbs.

7. The fixation system recited in claim 3, wherein the washer has a generally rectangular shape in axial cross section having two wings, a barb extending from each wing.

8. The fixation system recited in claim 3, wherein the washer has a generally circular shape in axial cross section and the barbs extend circumferentially about an edge thereof.

9. The fixation system recited in claim 3, wherein the washer has a generally rectilinear shape in axial cross section and the barbs extend from adjacent each corner thereof.

10. The fixation system recited in claim 3, wherein:
   the screw-type member has:
      a distal portion having a narrowing cross section toward a distal end, wherein in use an insertion of the screw-type member into soft tissue is facilitated by the narrowed distal end; and
      a variable-pitch helical protrusion along a central portion between a proximal end and the distal end, the helical protrusion having a helical pitch along the central portion, the helical pitch decreasing from the distal end to the proximal end; and
   the bore has a noncircular cross-sectional shape for permitting an elongated driving device having a noncircular cross-sectional shape to pass into the bore and to advance the screw-type member into the soft tissue by being rotated in a direction having a handedness commensurate with the helically shaped protrusion.

11. A system for fixing soft tissue within a bone tunnel comprising:
   a screw-type member having a proximal end, a distal end, and a bore extending at least partially therethrough from the proximal end, the screw-type member adapted for insertion against a first portion of soft tissue positioned within a bone tunnel, a second portion of the soft tissue emerging from the bone tunnel, the bore having a noncircular cross-sectional shape, the screw-type member further having a variable-pitch helical protrusion along a central portion between a proximal end and the distal end, the helical protrusion having a helical pitch along the central portion, the helical pitch decreasing from the distal end to the proximal end; and
   a tack member adapted to engage the screw-type member at the proximal end thereof, the tack member having means for restraining disengagement therewith, having a distal post portion dimensioned for insertion into the screw-type member bore and having a noncircular cross-section adapted for driving the screw-type member, the tack further having a barbed head portion extending outwardly beyond the post portion, the head portion having a plurality of barbs extending generally distalward for engaging and restraining a movement of the soft tissue piece.

12. The fixation system recited in claim 11, wherein the tack member head portion has means for being driven by a driver.

13. The fixation system recited in claim 11, wherein the restraining means comprises a protrusion extending outwardly from the post portion and the screw-type member bore has a protruding lip therein adapted to restrainingly engage the protrusion.

14. The fixation system recited in claim 13, wherein the protrusion comprises a plurality of generally proximally extending barbs.

15. The fixation system recited in claim 11, wherein the head has a generally rectangular shape in axial cross section having two wings, a barb extending from each wing.

16. The fixation system recited in claim 11, wherein the head has a generally circular shape in axial cross section and the barbs extend circumferentially about an edge thereof.

17. The fixation system recited in claim 11, wherein the head has a generally rectilinear shape in axial cross section and the barbs extend from adjacent each corner thereof.

18. The fixation system recited in claim 11, wherein:
   the screw-type member has:
      a distal portion having a narrowing cross section toward a distal end, wherein in use an insertion of the screw-type member into soft tissue is facilitated by the narrowed distal end.

19. A method for affixing a piece of soft tissue within a bone tunnel comprising the steps of:
   positioning a piece of soft tissue so that a portion thereof resides within a bone tunnel;
   positioning a first fixation member upon the piece of soft tissue within the bone tunnel;
   engaging a distal portion of a second fixation member with a proximal portion of the first fixation member;
   restraining a disengagement between the first and the second fixation members; and
   engaging a piece of the soft tissue outside the bone tunnel with an element at a proximal end of the second fixation member.

20. The method recited in claim 19, wherein:
   the first fixation member comprises a screw having a bore extending from a proximal end, the bore noncircular in axial cross section;
   the distal portion of the second fixation member comprises a post having a noncircular shape in axial cross section insertable into the screw bore; and
   the first fixation member positioning step comprises screwing the screw into the bone tunnel.

21. The method recited in claim 20, wherein:
   the second fixation member comprises a tack member having a distal post portion dimensioned for insertion into the screw member bore and a barbed head portion extending outwardly beyond the post portion, the head portion having a plurality of barbs extending generally distalward; and
   the soft tissue engaging step comprises impaling the soft tissue piece outside the bone tunnel with the barbs.

22. The method recited in claim 20, wherein:
   the second fixation member comprises a tack member having a distal portion comprising the post and a proximal head portion having a width greater than a width of the post portion;

the second fixation member engaging element comprises a barbed washer having a hole extending from a proximal face through to a distal face, the hole dimensioned for free rotation about the post and for retention by the tack head portion therebeneath, the distal face having a plurality of barbs extending generally distalward; and the soft tissue engaging step comprises impaling the soft tissue piece outside the bone tunnel with the barbs.

23. The method recited in claim 22, wherein:

the tack member post has a plurality of generally proximally extending barbs;

the screw bore has a lip extending thereinto; and the disengagement restraining step comprises inserting the post so that the post barbs extend distal of the lip.

24. A method for affixing a piece of soft tissue into a bone tunnel comprising the steps of:

positioning a piece of soft tissue with a first portion within a bone tunnel and a second portion extending therefrom;

inserting a cannula into a surgical site with a distal end positioned adjacent a hole in the bone and against the soft tissue second portion, the cannula having a doubly flared proximal portion;

inserting a screw having a head through a hole in a washer having distally protruding barbs from a pair of laterally extending wings adapted for retention within the cannula proximal portion, the washer dimensioned for axial retention by the screw head and for rotational freedom of motion about the screw distal portion;

inserting the screw and washer assemblage into the cannula;

driving the screw into the bone tunnel and against the soft tissue, the washer permitted to spin against the screw while being retained within the cannula proximal portion;

removing the cannula from the surgical site; and permitting the barbs to bear against the soft tissue second portion adjacent the tunnel.

25. A system for affixing a piece of tissue to a bone comprising:

a generally cylindrical cannula member adapted for insertion into a surgical site adjacent a tunnel in the bone;

a generally cylindrical screw member dimensioned for insertion through the cannula member, the screw member having a head at a proximal end and a bore extending at least partially therethrough from the proximal end, the bore having means for being driven by a driver; and a barbed washer having a hole extending from a proximal face through to a distal face, the hole dimensioned for free rotation about the screw member and for retention by the screw head therebeneath, the distal face having a plurality of barbs extending generally distalward for engaging and retraining a movement of a distal tissue piece, wherein the washer when engaged with the screw member is decoupled in at least one degree of freedom therefrom.

26. The system recited in claim 25, wherein:

the screw member has:

a distal portion having a narrowing cross section toward a distal end, wherein in use an insertion of the screw member into tissue is facilitated by the narrowed distal end; and a variable-pitch helical protrusion along a central portion between a proximal end and the distal end, the helical protrusion having a helical pitch along the central portion, the helical pitch decreasing from the distal end to the proximal end; and the bore has a noncircular cross-sectional shape for permitting a driver having a noncircular cross-sectional shape to pass into the bore and to advance the screw member into the distal piece of tissue by being rotated in a direction having a handedness commensurate with the helically shaped protrusion.

27. The system recited in claim 25, wherein:

the washer hole has a threaded portion; and the screw member has a threaded distal portion and a threaded proximal portion adjacent the head, the distal portion for engaging the tissue piece and the bone and the proximal portion for engaging the washer hole threaded portion.

28. The system recited in claim 27, wherein:

the washer comprises a flexible head having a pair of outwardly extending wings and a barb extending distal of each wing;

the cannula member has a doubly flared proximal portion dimensioned to house the washer head and prevent a rotation thereof.

29. A method of affixing a distal and a proximal piece of bone together comprising the steps of:

making a hole through the distal bone piece;

making a tunnel in the proximal bone piece;

inserting a cannula through the distal bone piece hole with a distal end positioned adjacent the tunnel in the proximal bone piece, the cannula having a doubly flared proximal portion;

inserting a screw having a head through a hole in a washer having distally protruding barbs from a pair of laterally extending wings adapted for retention within the cannula proximal portion, the washer dimensioned for axial retention by the screw head and for rotational freedom of motion about the screw distal portion;

inserting the screw and washer assemblage into the cannula;

driving the screw into the distal bone piece tunnel, the washer permitted to spin against the screw while being retained within the cannula proximal portion;

removing the cannula from the proximal bone piece hole; and permitting the barbs to bear against the proximal bone portion adjacent the tunnel.

* * * * *